United States Patent
Watanabe et al.

(10) Patent No.: US 6,764,695 B1
(45) Date of Patent: Jul. 20, 2004

(54) TABLET AND PROCESS FOR PRODUCING TABLETS

(75) Inventors: Yasushi Watanabe, Numazu (JP); Kiyoshi Morimoto, Mishima (JP); Yuji Iwase, Gotenba (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/806,761
(22) PCT Filed: Oct. 5, 1999
(86) PCT No.: PCT/JP99/05463
§ 371 (c)(1), (2), (4) Date: Apr. 3, 2001
(87) PCT Pub. No.: WO00/19983
PCT Pub. Date: Apr. 13, 2000

(51) Int. Cl.⁷ .............................. A61K 9/20; A61K 9/28
(52) U.S. Cl. ........................ 424/465; 424/464; 424/474
(58) Field of Search ................................ 424/464, 465, 424/474

(56) References Cited

U.S. PATENT DOCUMENTS 2,971,889 A  2/1961 Swintosky .................... 167/82
3,042,531 A * 7/1962 Leal et al. .................... 99/141
4,047,866 A * 9/1977 Shah ........................... 425/107

FOREIGN PATENT DOCUMENTS

| EP | 0 650 826 | 6/1997 |
| EP | 0 605 174 | 6/1998 |
| EP | 1 070 496 | 4/1999 |
| JP | 6-1717 | 1/1994 |
| JP | 9-104621 | 4/1997 |

* cited by examiner

Primary Examiner—James M. Spear
(74) Attorney, Agent, or Firm—Fitzpatrick Cella Harper & Scinto

(57) ABSTRACT

A tablet including active substance affected by lubricant, wherein the tablet is comprised of compressed mixture of active substance and adjuvant except for lubricant, and lubricant exists only on the surface of the tablet but is not included in the tablet. Such a tablet production method comprising the steps of producing mixture of active substance affected by lubricant and adjuvant, mixing lubricant powder with positive pulsating vibration air for dispersion, spraying the lubricant powder dispersed by the positive vibration air on a lower surface of an upper punch, an upper surface of a lower punch and an inner circumferential wall of a die, and tabletting the mixture by means of the upper and lower punches and the die.

7 Claims, 6 Drawing Sheets

(a)

(b)

(c)

TABLET AND PROCESS FOR PRODUCING TABLETS

This application is a 371 of PCT/JP99/05463 filed Oct. 05, 1999.

TECHNICAL FIELD

The present invention relates to a tablet and a tablet production method, specifically to a tablet of which active substance (namely medicament) is kept stably without being affected by lubricant in case active substance is colored, decomposed or deteriorated in its potency, when such active substance touches lubricant, and to its production method.

BACKGROUND ART

A tablet is a widely used because it is convenient for carrying and dosing and is easy to be taken for an elder person or a child because it doesn't float on the water when dosing with water.

Lubricant powder other than active substance powder, adjuvant powder and so on is added in molding material (powdered or granular material) to be compressed and tabletted in order to prevent grinding between punches and dies of a molding machine while tabletting and to prevent tabletting problems such as sticking, laminating and capping of produced tablets.

The present inventors have found that some active substances are colored, decomposed or deteriorated in their potencies when such active substances touch lubricant.

In order to avoid such phenomenon, it can be expected to tablet molding material without adding lubricant. However, grinding between punches and dies of a molding and tabletting problems such as sticking, laminating and capping of produced tablets are caused and as a result continuous tabletting can't be executed.

Therefore, under the present situation, lubricant is usually added in molding material giving a preference to industrial production basis even though a tablet is colored or stability of active substance in a tablet is deteriorated.

However, it isn't desirable because colored tablet causes a patient and health personnel such as a doctor and a pharmacist anxiety when such a tablet can be observed from outside like a naked tablet. Further, when potency of active substance in a tablet is deteriorated, objective clinical effect of the tablet may not be adequately brought out.

DISCLOSURE OF INVENTION

The present invention has been proposed to solve the above-mentioned problems. The object of the invention is to provide a tablet in which active substance doesn't touch lubricant and grinding between punches and dies of a molding machine and tabletting problems such as sticking, laminating and capping when producing tablets aren't caused in case active substance included in the tablet is colored, decomposed or deteriorated in its potency when such active substance touches lubricant and to provide a method for producing such a tablet.

According to the tablet of the present invention, it includes active substance affected by lubricant and is comprised of compressed mixture of active substance and adjuvant except for lubricant, and lubricant exists only on the surface of the tablet but isn't included in the tablet.

The term "active substance affected by lubricant" in this specification means active substance which is colored, decomposed or deteriorated in its potency when such active substance touches lubricant.

It is difficult to specify such active substance, however, it includes active substances of which coloring degree of a mixture of active substance, adjuvant except for lubricant, and lubricant after a fixed time is larger than that of a mixture of active substance and adjuvant except for lubricant comparing with that at a start time, or content of active substance in a mixture of active substance, adjuvant except for lubricant, and lubricant after a fixed time is larger than that in a mixture of active substance and adjuvant except for lubricant comparing with that at a start time when coloring degree test (absorbance analysis, color analysis and so on) and stability test are performed respectively.

Further, "active substance affected by lubricant" includes active substance which is affected by moisture in air, proton and so on produced in a tablet, and lubricant.

The term "adjuvant except for lubricant" in this specification is material used for producing a tablet and means material other than lubricant.

More specifically, "adjuvant except for lubricant" may include excipient (filler) for increasing the amount for facilitating handling and for giving required volume as pharmaceutical drugs, binder, disintegrator, and other substance if required, except for lubricant.

"Lubricant" in this specification includes lubricant in narrow sense which is added in molding material for dispersing force applied between powdered particle of molding material at a time of compression (tabletting) and for preventing adhering of powdered material on the punches and dies of a tabletting machine, and also includes glidants which is added in molding material for improving fluidity of molding material.

Such lubricant isn't limited if it is usually used and may include light anhydrous silicic acid, stearic acid, and stearic acid metal salt.

Preferable examples of lubricants are stearic acid metal salt (Mg salt, Ca salt, Al salt, K salt, Na salt) and metal salt such as hydrated aluminum silicate, preferable examples of glidants are metal salt (oxide) such as talc and so on.

The lubricant existing on the surface of the tablet isn't applied on purpose. A part of lubricant applied on the surfaces of the punches and the dies of the tabletting machine used for tabletting is attached on the surface of the tablet at the time of compressing.

As such a tablet doesn't include lubricant therein, the active substance included in the tablet doesn't touch lubricant. Therefore, the active substance isn't colored, decomposed or its potency isn't deteriorated so that the active substance can show high stability.

According to the tablet of the present invention, the active substance affected by lubricant is chemical substance having functional group.

The term "functional group" in this specification includes carboxyl group, amino group, hydroxyl group, ester group, amide group, phosphate group, carbonyl group, sulfonyl group, sulfonyloxy group, guanidyl group, sulfonamide group, halogen (chlorine, fluorosis, iodine, bromine and so on) and so on.

If lubricant is above-mentioned metal salt and active substance having such functional group touches the lubricant, the active substance reacts with metal component (magnesium, calcium and so on) of the lubricant so that it is colored, decomposed or its potency is deteriorated.

However, as the tablet doesn't include lubricant therein, active substance, namely chemical substance having functional group doesn't touch the lubricant. Therefore, the active substance included in the table is stably kept without being colored, decomposed or deteriorating its potency.

According to the tablet in the present invention, the active substance affected by lubricant may be one of ascorbic acid and acetylsalicylic acid.

Ascorbic acid and acetylsalicylic acid are accelerated to be decomposed and colored by stearic acid metal salt (Mg salt, Ca salt), hydrated aluminum silicate, and talc. However, as the tablet doesn't include lubricant therein, ascorbic acid and acetylsalicylic acid included in the tablet doesn't touch the lubricant. Therefore, ascorbic acid and acetylsalicylic acid in the tablet aren't colored, decomposed or their potency isn't deteriorated so that the active substance can be kept stably.

According to the tablet in the present invention, a formulation of the active substance is granule, a formulation of the adjuvant except for lubricant is granule, and the active substance granule and the adjuvant granule are substantially same in particle diameter.

The term "granule" in this specification is a granulated material in which powdered material is grown to be with a fixed particle diameter using binder according to a fluid-bed granulation method.

The phrase "the active substance granule and the adjuvant granule are substantially same in particle diameter" more specifically means that the average particle diameter and the particle size distribution of the active substance granule and the adjuvant granule are substantially same.

As a mixture of active substance granule and adjuvant granule, not a mixture of active substance powder and adjuvant powder, is compressed, active substance granule and/or adjuvant granule are deformed or broken so that mechanical force applied therein can be dispersed.

Therefore, pressure caused by compressing doesn't concentrate on active substance granule so that tabletting can be achieved without denaturing the active substance even if physical property and chemical property of the active substance is apt to be denatured by high pressure.

As the particle diameter of the active substance granule and that of the adjuvant granule in the tablet are substantially same, those granules are spontaneously mixed uniformly in mixing process.

Further, when the mixture is filled in the die to which a lower punch is inserted to a fixed position at a material charge point of a rotary type tabletting machine, active substance granule doesn't substantially cause particle segregation in the mixture filled in the die.

Namely, active substance granule is homogeneously dispersed in a tablet.

Therefore, such a tablet is superior as a dividable tablet.

The tablet production method of the present invention comprises the steps of producing mixture of active substance affected by lubricant and adjuvant except for lubricant, mixing lubricant powder with positive pulsating vibration air for dispersion, spraying the lubricant powder dispersed by the positive vibration air on a lower surface of an upper punch, an upper surface of a lower punch and an inner circumferential wall of a die, and tabletting the mixture by means of the upper and lower punches and the die.

The term "pulsating vibration air" in this specification means air of which pressure is changed in time.

More specifically, "pulsating vibration air" means air wave of which high pressure part (peak) and low pressure part (valley) are alternately shown at a fixed period.

The term "positive pressure" in this specification means that air pressure in the tablet production system used in the present invention is higher than atmospheric pressure out of the system.

The term "positive pulsating vibration air" may include pulsating vibration air of which both peak and valley are positive and pulsating vibration air of which peak is positive pressure and valley is substantially equal to the atmospheric pressure out of the tabletting machine.

When positive pulsating vibration air is used for mixing lubricant powder with air for dispersion, lubricant powder is well dispersed by air comparing with the case when lubricant powder is dispersed by air having constant pressure.

Thus according to the tablet production method of the present invention, as lubricant powder dispersed by positive pulsating vibration air for dispersion is sprayed on the lower surface of the upper punch, the upper surface of the lower punch and the inner circumferential die wall, lubricant powder is uniformly applied thereon.

As a result, even if lubricant isn't added in the molding material, grinding between the upper punches, the lower punches, and the dies while tabletting and tabletting problems such as sticking, laminating, capping and so on aren't caused.

Therefore, according to such a tablet production method, a tablet which isn't colored and doesn't cause any deterioration of the potency of the active substance contained in the tablet during a storage of the tablet can be easily produced in case such active substance contained in the tablet is affected by lubricant, because lubricant isn't required to be added in molding material.

According to the tablet production method of the present invention, the spraying step is comprised of substantially vertically spraying at a blast the lubricant powder dispersed by the positive pulsating vibration air onto the upper surface of the lower punch when the lower punch is inserted in a predetermined position of the die, producing upward air flow directing substantially vertically for the lower surface of the upper punch around the lower surface of the upper punch, and gradually spraying the lubricant powder dispersed by the positive pulsating vibration air onto the lower surface of the upper punch while carrying the lubricant powder by the air flow.

According to such a tablet production method, lubricant powder dispersed by positive pulsating vibration air is sprayed at a blast on the upper surface of the lower punch on which extra lubricant is apt to be piled by gravitation so as to shorten the time for exposing the upper surface of the lower punch to lubricant powder. Further, extra lubricant powder piled on the upper surface of the lower punch by gravitation is blown out from the upper surface of the lower punch. Therefore, powder lubricant is uniformly applied on the upper surface of the lower punch.

Moreover, as part of lubricant blown from the upper surface of the lower punch is designed to be attached on the inner circumferential wall of the die into which the lower punch is inserted at a predetermined position, almost the same amount of lubricant as the amount applied on the upper surface of the lower punch is uniformly attached on the inner circumferential wall of the die on which lubricant has difficulty to be applied comparing with the upper surface of the lower punch.

As for the lower surface of the upper punch on which lubricant powder is difficult of applying, air flow going upward in almost vertical direction against the lower surface of the upper punch is generated around the lower surface of the upper punch.

Therefore, lubricant powder dispersed by positive pulsating vibration air flow sequentially runs into the lower surface of the upper punch to be applied thereon carrying the lubricant powder by the upward air flow.

Further according to the tablet production method, the lower surface of the upper punch is designed to be exposed in lubricant powder longer comparing with the upper surface of the lower punch. Almost the same amount of lubricant powder is uniformly applied on the lower surface of the upper punch by adjusting the exposure time like the upper surface of the lower punch, and the inner circumferential die wall.

Thus almost the same amount of lubricant powder is uniformly applied on the lower surface of the upper punch, the upper surface of the lower punch, and the inner circumferential die wall, so that molding material doesn't adhere on the punches and dies while tabletting if lubricant isn't added in the molding material. As a result, because grinding between punches and dies of a molding machine and tabletting problems such as sticking, laminating and capping of produced tablets are further prevented, continuous tabletting of molding material can be more completely achieved and a tablet without containing lubricant therein can be produced at high productivity.

Therefore, as a tablet without containing lubricant therein can be produced easily and at high productivity according to the present invention, the tablet which isn't colored, or deteriorated in its potency during the storage of the tablet even if active substance contained in the tablet is affected by lubricant.

BEST MODE FOR CARRYING OUT THE INVENTION

The present invention will be detailed hereinafter referring to the attached drawings.

Figure 1:
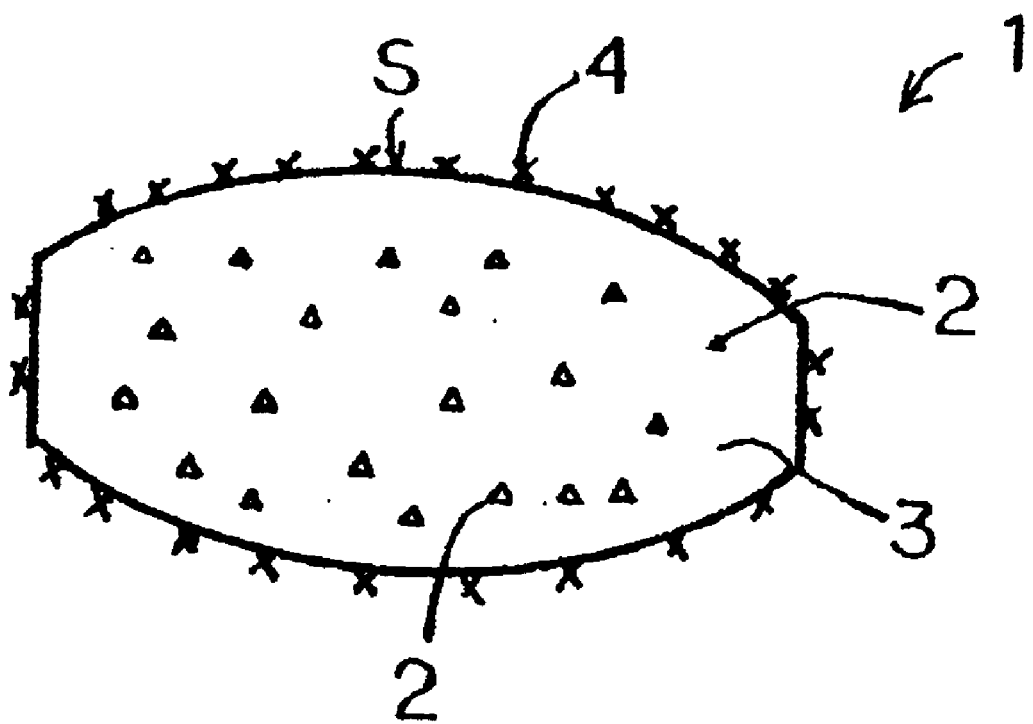
FIG. 1 is a sectional view showing a tablet of the present invention.

FIG. 1 is a sectional view showing a tablet of the present invention.

A tablet 1 includes active substance 2 * and adjuvant except for lubricant 3 * therein.

The tablet 1 has lubricant 4 *** only on its surface S.

The active substance 2 * is affected by lubricant 4 *.

The active substance 2 may be powder, preferably granule (granulated material).

More concretely, the active substance 2 is chemical substance having functional group.

Such chemical substance having functional group includes chemical substance with carboxyl group, amino group, hydroxyl group, ester group, amide group, phosphate group, carbonyl group, sulfonyl group, sulfonyloxy group, guanidyl group, sulfonamide group or halogen (chlorine, fluorosis, iodine, bromine and so on).

The compound thereof includes aspirin (acetylsalicylic acid) and ascorbic acid.

The adjuvant except for lubricant 3 *** may include excipient (filler) used for the purpose of giving required volume so as to facilitate preparation, binder, disintegrant and other substance if required, except for lubricant.

The adjuvant (except for lubricant) 3 *** may be powder, preferably granule (granulated material).

The adjuvant (except for lubricant) 3 *** may be organic or inorganic.

Organic adjuvant except for lubricant includes sugar or sugar alcohol such as lactose, sucrose, glucose, mannitol, D-sorbitol sugar, starch or starch derivatives such as corn starch, potato starch, α starch (NF pregelatinized starch), dextrin, carboxymethyl starch, cellulose such as micro crystalline cellulose, low substituted hydroxypropylcellulose, nternal cross-linked carmellose sodium, acacia gum, dextran, and pullulane.

Inorganic adjuvant except for lubricant include hydrated silicic acid such as light anhydrous silica acid.

Binder isn't limited and includes well-known micro crystalline cellulose, starch, acacia gum, gelatin, saccharide (sucrose, mannitol), methylcellulose, ethylcellulose, carmellose sodium, hydroxypropylcellulose, hydroxypropylmethylcellulose, polyvinylpyrrolidone.

Disintegrant isn't limited and includes well-known agar powder, gelatin powder, unmodified starch (for example corn starch and so on), cellulose derivatives (for example micro crystalline cellulose, low substituted hydroxypropylcellulose, bridged polyvinylpyrrolidone and so on).

Further, coloring agent (such as water-soluble edible synthetic color) which is admitted to be added by law may be included as an adjuvant except for lubricant.

Here, a production method of the tablet 1 is explained hereinafter.

The embodiment in which a mixture of active substance granule 2 * and adjuvant granule (except for lubricant) 3 * is compressed to produce the tablet 1 is explained hereinafter.

According to well-known fluid-bed granulation method, active substance granule 2 * having prescribed average particle diameter and prescribed particle size distribution and adjuvant granule (except for lubricant) 3 * having prescribed average particle diameter and prescribed particle size distribution are produced.

It is preferable that active substance granule 2 * and adjuvant granule 3 * are granulated so as to have almost the same average particle diameter and particle size distribution.

The active substance granule 2 * and adjuvant granule 3 * are mixed by a well-known mixing machine.

When the particle diameters of the active substance granule 2 * and the adjuvant granule 3 * are substantially same, such powder can be uniformly mixed in the course of nature.

Then thus produced mixture are compressed to be produced as tablet.

Figure 2:
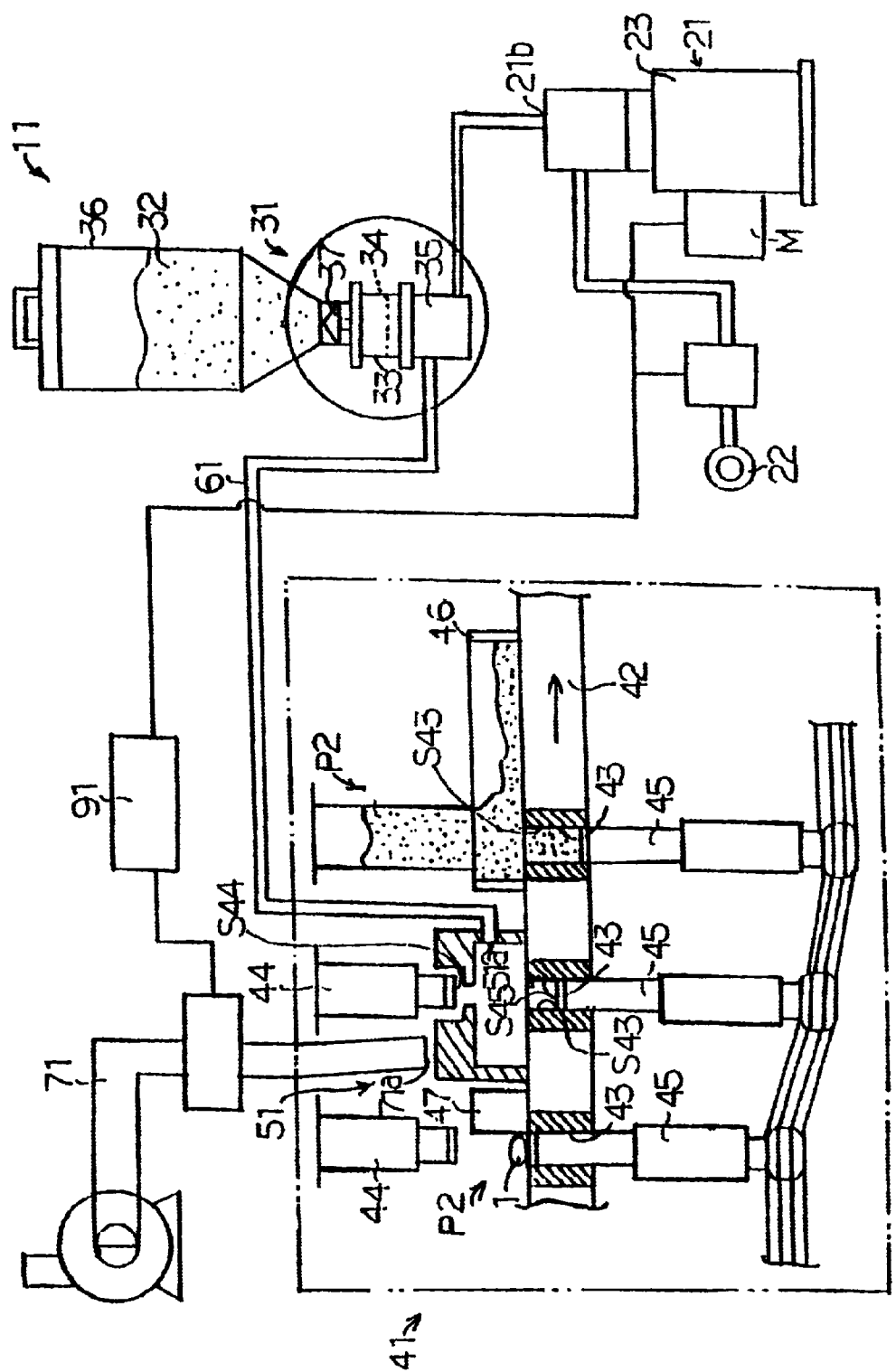
FIG. 2 shows whole construction of the tablet production system preferable to produce a tablet according to the present invention.

FIG. 2 shows whole construction of the tablet production system preferable to produce a tablet according to the present invention.

The tablet production system (tabletting machine with lubricant spray means) 11 is provided with a high pressure pulsating vibration air generation means 21, a dry type powder spray means 31, a rotary type tabletting machine 41, and a lubricant spray means 51.

A discharge port 21b for high pressure pulsating vibration air of the high pressure pulsating vibration air generation means 21 and a lubricant introduction port 51a of the lubricant spray means 51 are connected by an air transport pipe 61.

Figure 4:
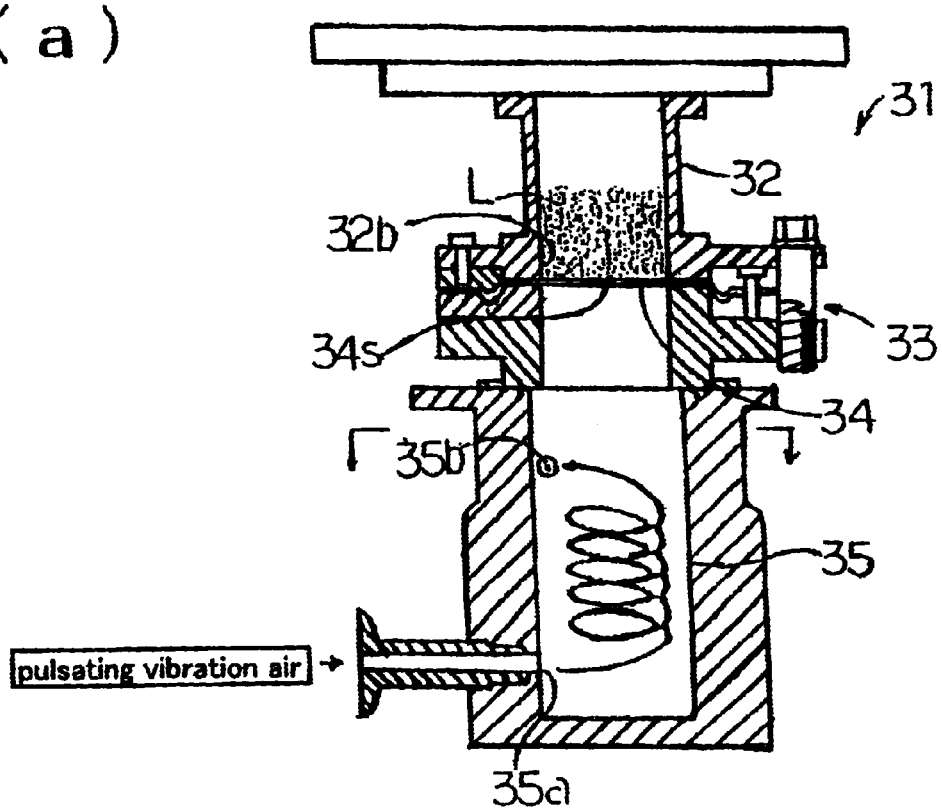
FIG. 4 illustrates schematic construction of dry type powder spray means.
Figure 4:
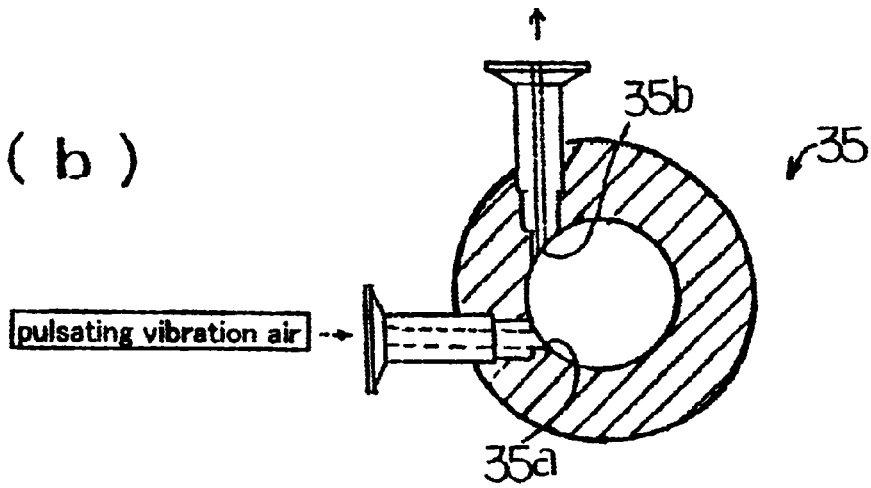

A container (container 35 as shown in FIG. 4) is interposed in the air transport pipe 61.

The container 35 is connected to a discharge port 32b of a lubricant storage tank 32 of the dry type powder spray means 31 via a lubricant supply means 33.

Next, the high pressure pulsating vibration air generation means 21 is detailed.

Figure 3:
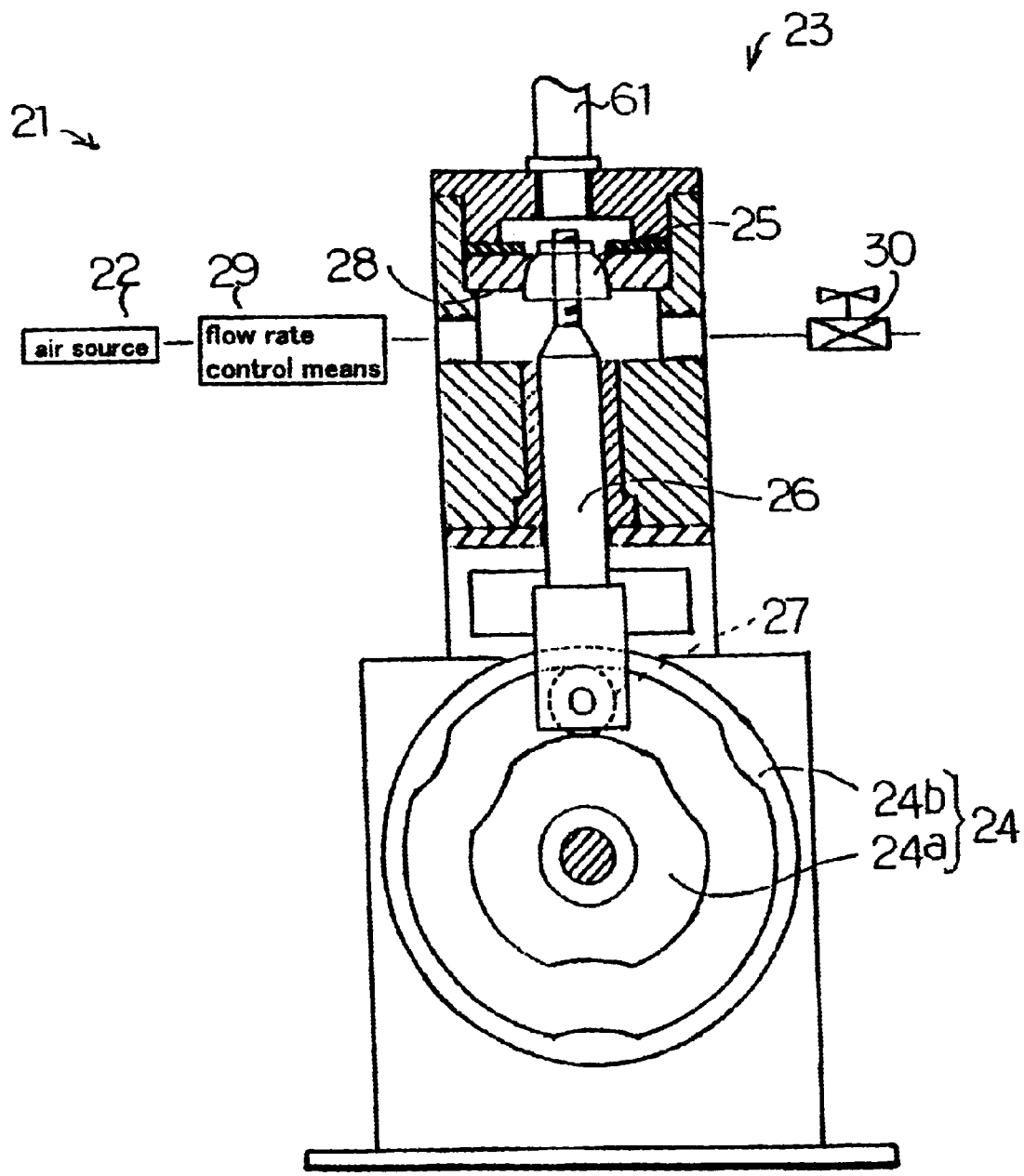
FIG. 3 illustrates schematic construction of high pressure pulsating vibration air generation means.

FIG. 3 illustrates schematic construction of high pressure pulsating vibration air generation means 21.

The high pressure pulsating vibration air generation means 21 comprises with an air source 22 such as blower and a pulsating vibration air generation means 23 for changing high pressure air generated by the air source 22 to pulsating vibration air, as shown in FIG. 3.

The pulsating vibration air generation means 23 is provided with a guide rail means 24 formed cylindrical and having concavo-convex pattern and a valve 25.

When the cylindrical guide rail means 24 is rotated, the valve 25 is designed to move up and down along the concavo-convex pattern provided for the guide rail means 24 so as to open and close the air transport pipe 61.

The member M shown in FIG. 2 is an electric motor for rotating the guide rail means 24.

The valve 25 is designed to control the air transport pipe 61 such as full-open, half-open, or full-closed, and so on by moving up and down according to the concavo-convex pattern.

A rotary roller 27 is provided at the bottom of a shaft 26 of the valve 25.

The guide rail means 24 is provided with an upper rail means 24a and a lower rail means 24b and the rotary roller 27 is rotatably sandwiched between the upper rail means 24a and the lower rail means 24b. Therefore, the valve 25 can be accurately operated along the concavo-convex pattern without jumping out of the guide rail means 24.

The operation of the valve 25 of the pulsating vibration air generation means 23 is regulated so as to be most appropriate, taking physical property of lubricant powder into consideration in this embodiment.

The concavo-convex pattern provided for the guide rail means 24 is also regulated in such a manner that the operation of the valve 25 is made most appropriate, taking physical property of lubricant powder in consideration.

The pressure of the air source 22 is also regulated taking physical property of lubricant powder in consideration.

Further, the rotary speed of the guide rail means 24 is regulated taking physical property of lubricant powder into consideration.

As pulsating vibration air is apt to be attenuated, it is required to form off (valley) condition at first and to complete full-closed condition of the valve 25 and a plug receiver 28. Also it is required to produce clear pulsating vibration air in which full-closed condition, half-open condition, and full-open condition and so on are apparently distinguished.

For this purpose, it is preferable, for example, the valve receiver 28 is shaped like a concaved ball, reverse shape of the valve 25 when the valve 25 is formed like a bell of which tip end is narrowed so as to keep airtight between the valve 25 and the plug receiver 28 when the valve 25 is moved up and down and closes the receiver 28.

The member 29 in FIG. 3 shows a flow control means for adjusting compressed air flow generated from the air source 22 and the member 30 shows a control valve for adjusting pressure of positive pulsating vibration air to be supplied to the air transport pipe 61.

Next, a dry type powder spray means is explained.

FIG. 4 illustrates schematic construction of dry type powder spray means.

The dry type powder spray means 31 is provided with a lubricant storage tank 32 and a lubricant supply means 33.

Lubricant powder L is stored in the lubricant storage tank 32.

The lubricant supply means 33 is provided for the discharge port 32b of the lubricant storage tank 32 and is constructed with an elastic membrane 32 having a slit 34s.

When positive pulsating vibration air generated from the high pressure pulsating vibration air generation means 21 is fed in the container 35 provided under the elastic membrane 34, the elastic membrane 34 is vibrated up and down and the slit 34s is opened and closed so that lubricant powder L stored in the storage tank 32 is discharged from the discharge port 32b of the storage tank 32.

The container 35 is connected to the lubricant storage tank 32 via the lubricant supply means 33.

When pulsating vibration air is fed in the container 35, pressure in the container 35 is changed and the elastic membrane 34 is elastically deformed up and down according to pulsating vibration air fed in the container 35.

Figure 5:
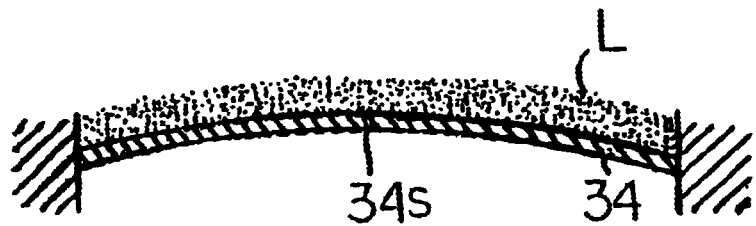
FIG. 5 illustrates operational principle of lubricant supplying means.
Figure 5:
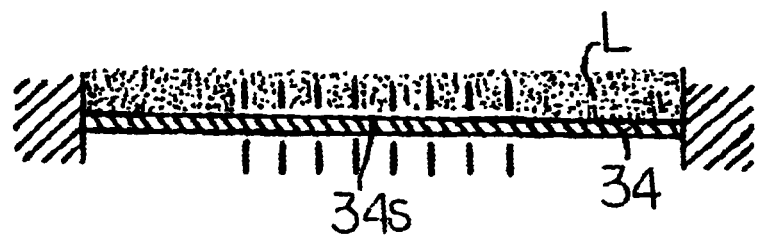
Figure 5:
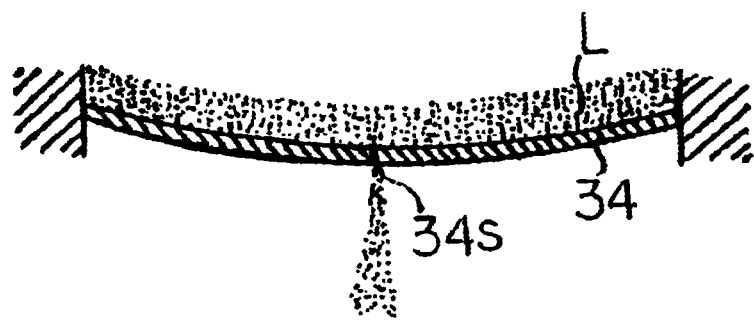

FIG. 5 illustrates operational principle of lubricant supplying means 33.

When positive pulsating vibration air fed in the container 35 is at its peak and the pressure in the container 35 becomes high, the elastic member 34 is elastically deformed in such a manner that its center is moved upward as shown in FIG. 5(a) and the slit 34s is opened like a letter V.

Lubricant powder L drops in the V-shaped opening of the slit 34s.

When positive pulsating vibration air moves to its valley and the pressure in the container 35 is lowered, the elastic membrane 34 is returned to its original shape as shown in FIG. 5(b), the lubricant L dropped when the slit 34s is opened is kept therein.

When positive pulsating vibration air is at its valley and the pressure in the container 35 becomes low, the center of the elastic membrane 34 is moved downwardly as shown in FIG. 5(c) and the slit 34s is opened reverse V shaped.

In this time the lubricant powder L kept in the slit 34s is dropped in the container 35 to be dispersed by pulsating vibration air supplied in the container 35.

Thus when pulsating vibration air is constant, the membrane 34 is always constantly deformed. Therefore, fixed amount of lubricant powder L is discharged in the container 35.

Further according to the dry type powder spray means 31, the container 35 under the elastic membrane 34 is provided with an air introduced port 35a for supplying pulsating vibration air in the container 35 and an air discharge port 35b for feeding lubricant powder L dispersed by air to the lubricant spray means 51.

The air introduction port 35a is provided under the container 35 in approximately tangential direction of the container 35.

The air discharge port 35b is provided above the position where the air introduction port 35a is provided in approximately tangential direction of the container 35.

According to the dry type powder spray means 31, as the air introduction port 35a and the air discharge port 35b are provided like the above-mentioned position and direction, pulsating vibration air becomes circular flow having characteristic of pulsating vibration air directing from the air introduction port 35a to the air discharge port 35b.

Large particle among the lubricant powder L discharged into the container 35 from the lubricant storage tank 32 is destroyed because of the circular flow of pulsating vibration air.

Further, as size classification function is caused like cyclone in the container 35 because of the circular flow of pulsating vibration air, the lubricant powder L supplied in the container 35 is sized into a fixed particle diameter and fed to the lubricant spray means 51.

Furthermore, large particle of lubricant powder L isn't accumulated in the container 35 and such large particle is destroyed by circular flow to be fed in the lubricant spray means 51 so that lubricant powder L is efficiently used.

Although it isn't shown in FIG. 4, actually a hopper for storing lubricant powder L (see the hopper 36 in FIG. 2) is connected to the lubricant storage tank 32 of the dry type powder spray means 31 via a material supply valve (see material supply valve 37 in FIG. 2). The lubricant storage tank 32 is made of light permeable material such as glass or resin like acrylic resin and is provided with a level sensor (not shown) fixed distance above the lubricant supply means 33, namely the elastic membrane 34. The level sensor is provided with light emitting element (not shown) and light receiving element (not shown) and both elements are opposed so as to sandwich the lubricant storage tank 32.

The dry type powder spray means 31 is automatically controlled such that the light emitting element (not shown) of the level sensor is lightened when powder is discharged in the container 35 from the slit 34s of the elastic membrane 34 by means of positive pulsating vibration air, the material supply valve 36 is opened when the light receiving panel element (not shown) receives light emitted form the light emitting element (not shown), and the material supply valve 36 is closed when the light receiving element (not shown) comes not to receive light from the light emitting element (not shown). Consequently a fixed amount of lubricant powder L is always contained in the lubricant storage tank 32 and a fixed amount of lubricant powder L is discharged in the container 35 from the slit 34s of the elastic membrane 34 more accurately when positive pulsating vibration air is constant.

Next, a rotary type tabletting machine is explained.

According to the tablet production system 11, a well-known rotary type tabletting machine 41 is used.

Namely, a rotary type tabletting machine 41 as shown in FIG. 2 is used in the tablet production system, comprising a rotary table 42 having plural dies 43 •••, plural upper punches 44 ••• provided corresponding to the plural dies 43 ••• of the rotary table 42 respectively and rotatable synchronized with rotational speed of the rotary table 42, plural lower punches 45 ••• provided corresponding to the plural dies 43 ••• of the rotary table 42 respectively and rotatable synchronized with rotational speed of the rotary table 42, and so on.

According to this system 11, at material charge point P1, molding material is sequentially charged in the die 43 which is moved to a charge point by the rotation of the rotary table 42 and in which the lower punch 45 is inserted at a fixed position in the die 43, material is scraped by a scraper 46 so as to adjust the amount of molding material in the die 43. Then at a tabletting position (not shown), the molding material is compressed by means of the upper punch 44, the lower punch 45 and the die 43. At a tablet discharge point P2, the tablet 1 is sequentially removed to a fixed place by means of a guide plate 47.

As explained, although a well-known rotary type tabletting machine 41 is used in the system 11, it is characterized in that a lubricant spray means is newly provided. So such a spray means is explained hereinafter.

Figure 6:
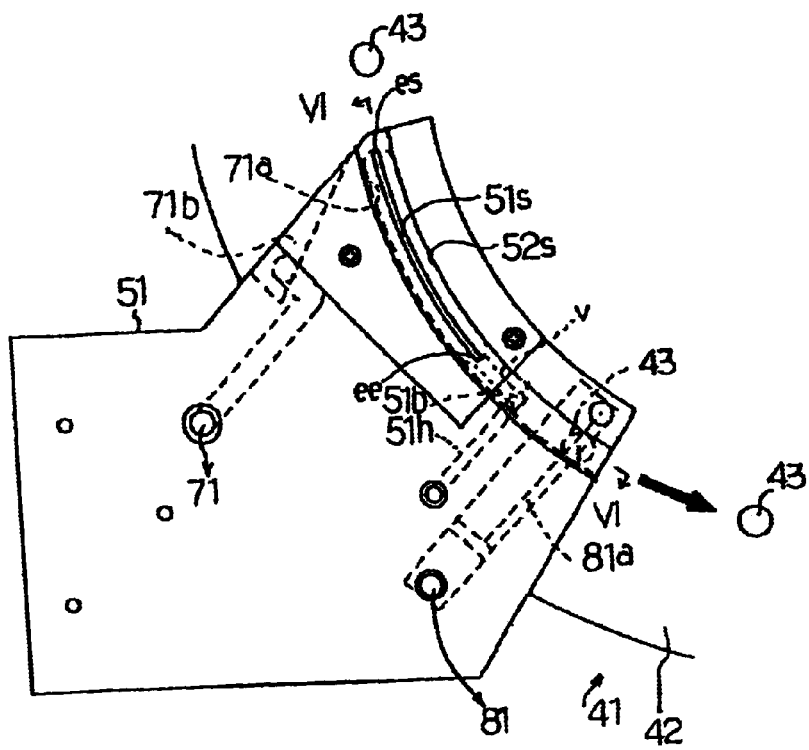
FIG. 6 illustrates schematic construction of lubricant spray means.
Figure 6:
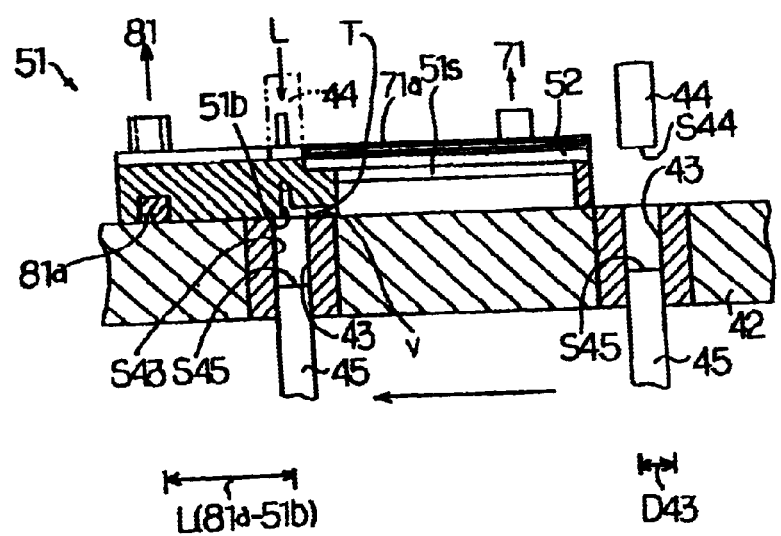

FIG. 6 illustrates construction of lubricant spray means. FIG. 6(a) is a flat view of the lubricant spray means and FIG. 6(b) is a sectional view along the line VI—VI in FIG. 6(a).

The lubricant spray means 51 is fixedly provided for a predetermined position of the rotary table 42 of the rotary type tabletting machine 41.

The bottom of the lubricant spray means 51 contacts the rotary table 42 and the rotary table 42 is constructed so as to be slidable along the bottom.

The lubricant spray means 51 has a lubricant introduction port 51a for receiving lubricant powder L dispersed by air at the outer surface thereof.

The lubricant powder L supplied from the lubricant introduction port 51a and dispersed by positive pulsating vibration air is sent to the surface (bottom) of the lubricant spray means 51 facing the rotary table 42 through a penetrating hole 51h passing through the lubricant spray means 51 and is sprayed to an upper surface S45 of the lower punch 45 inserted at a predetermined position in the die 43 of the rotary table 42 from a discharge port 51b of the penetrating hole 51h.

The position for spraying lubricant powder on the upper surface S45 of the lower punch 45 is expediently defined as lubricant spraying point.

In this embodiment, lubricant powder dispersed by air is sprayed on the upper surface S45 of the lower punch 45 approximately vertical direction from the discharge port 51b of the penetrating hole 51h.

A groove v is provided for the surface (bottom) of the lubricant spray means 51 and is positioned at the opposite side to the rotational direction of the rotary table 42 from the discharge port 51b of the penetrating hole 51b.

Extra lubricant powder L accumulated on the upper surface S45 of the lower punch 45 is blown off by the air supplied with lubricant powder L and a part of lubricant blown off from the upper surface S45 is designed to attach on the circumferential side S43 of the die 43.

Further the lubricant powder L is designed to be sent to a direction opposite to the rotational direction of the rotary table 42 via a pipe T together with air sent together with lubricant powder L, the pipe T being formed by the combination of both the groove v provided on the surface (bottom) of the lubricant spray means 51 and the surface of the rotary table 42.

The edge of the groove v provided for the surface (bottom) of the lubricant spray means 51 is connected to a slit 51s is provided so as to penetrate the lubricant spray means 51.

At the outer surface of the lubricant spray means 51 an upper punch accommodating part 52 is provided along the rotation or bit of the upper punch 44 ••• for sequentially accommodating the upper punch 44 ••• rotating synchronized with rotation of the rotary table 42 along the slit 51s.

A suction port 71a of the air suction means 71 such as blower for generating air flow is provided above the slit 51s.

When a suction port (71b shown as dotted line in FIG. 6(a)) is provided at the bottom of the lubricant spray means 51 (the surface facing the surface of the rotary table 42) and the air suction means 71 for generating air flow is driven, it is designed such that suction mode flow directing the air suction port 71a around the suction port 71a and suction mode flow directing into the air suction port 71b can be generated. Molding material attached on the rotary table 42 can be removed by the suction mode flow directing the suction port 71b.

The size of the suction port 71a of the air suction means 71 for generating air flow is designed so as to cover the whole slit 51s and so as to be similar to the shape of the slit 51s.

As a result, when the air suction means 71 for generating air flow is driven, air flow directing from downward to upward can be generated uniformly and evenly between an end es to the other end ee of the slit 51s.

Thus, lubricant powder L can be slowly attached on the lower surface S44 of the upper punch 44 on which lubricant L has difficulty to be attached by gravity while the upper punch 44 is moved from the end es to the other end ee of the slit 51s in the upper punch accommodating part 52.

Further this embodiment is provided with a lubricant suction means 81 for removing extra lubricant powder L overflown on the surface of the rotary table 42 or attached on the upper surface S45 of the lower punch 45 and the circumferential wall S43 of the die 43 at the downstream of the lubricant spraying point (upstream of the molding material charge point).

The lubricant suction means 81 is comprised of a blower and so on, a suction port 81a is formed like a slit (rectangular) of which longitudinal direction faces to an approximate center from the circumference of the rotary table 42, and the suction part 81a is designed to cover the die 43.

Therefore, when the lubricant suction means 81 is driven, the area of the rotary table 42 around the die 43 is always kept clean. As a result, the lubricant powder L attached on the rotary table 42 around the die 43 doesn't drop into the dies 43 so that a tablet without including lubricant powder L therein can be continuously tabletted.

As extra lubricant powder L isn't attached on the upper surfaces S45 of the lower punches 45 and the circumferential walls S43 of the dies 43, a tablet having minimum lubricant on its surface can be produced.

The suction port 81a of the lubricant suction means 81 is preferably provided adequately apart from the discharge port 51b so as not to communicate the suction port 81a and the discharge port 51b by means of dies 43 ••• moving under the lubricant spray means 51 according to the rotation of the rotary table 42.

More concretely, if the distance between the suction port 81a and the discharge port 51b is defined as L (81a–51b) and the diameter of the dies 43 ••• is defined as D43, the distance L is preferably set longer than the diameter D43 (L (81a–51b)>D43).

When the suction port 81a of the lubricant suction means 81 is thus provided adequately apart from the discharge port 51b so as not to communicate the suction port 81a and the discharge port 51b by means of dies 43 ••• moving under the lubricant spray means 51 according to the rotation of the rotary table 42, spraying condition of lubricant powder sprayed from the discharge port 51b isn't affected at all even if suction force of the suction port 81a is changed by varying driving amount of the lubricant suction means 81. Therefore, the driving amount of the lubricant suction means 81 can be changed so as to be appropriate for removing extra lubricant powder attached around the dies 43 ••• of the rotary table 42 without considering spraying condition of the lubricant powder sprayed from the discharge port 51b. Further, it can be changed so as to be appropriate for removing extra lubricant powder attached on the circumferential surfaces S43 ••• of the dies 43 ••• or the upper surfaces S45 ••• of the lower punches 45 •••.

The member 91 in FIG. 2 indicates an operation unit for controlling the whole tablet production system 11.

The operation unit 91 is provided with an input device for setting operational environment of the system 11.

The input device adopts touch panel system integrating a display and an operation panel.

The operational environment of the tablet production system 11 can be set by selecting a menu panel.

Each menu panel corresponds to each hierarchical stage of plural tree structured stages.

Next the production method of the tablet 1 with the tablet production system 11 is explained. The tablet 1 is constructed such that active substance 2 affected by lubricant 4 is included, lubricant 4 isn't included in the tablet, and lubricant 4 only exists on the surface of the tablet 1. The tablet 1 is produced by compressing a mixture of active substance 2 and adjvant (except for lubricant) 3.

At first operational condition is input to the operation unit 91.

And lubricant powder L is stored in the lubricant storage tank 32 of the dry type powder spray means 31.

Then the high pressure pulsating vibration air generation means 21 is driven under the operational condition input by the operation unit 91.

Positive pulsating vibration air generated from the high pressure pulsating vibration air generation means 21 is fed to the container 35 provided under the elastic membrane 34 of the dry type powder spray means 31 so as to vibrate the elastic membrane 34 up and down.

The shape of the slit 34s formed on the elastic membrane 34 changes "V-shaped"→"close"→"reverse V-shaped" repeatedly by vibrating the elastic membrane 34 up and down. Therefore, the lubricant L stored in the lubricant storage tank 32 is discharged to the container 35.

As the discharge condition can be defined by the condition of pulsating vibration air fed in the container 35, lubricant amount discharged to the container 35 per time is made constant if pulsating vibration air is kept constant.

The lubricant powder L discharged in the container 35 is dispersed by pulsating vibration air in the container 35.

Further according to the dry type powder spray means 31, as pulsating vibration air is designed to be circulated in the container 35, large particle of the discharged lubricant powder L in the container 35 is destroyed into small particle by the circulation.

Then lubricant powder L having substantially same particle diameter is fed to the lubricant spray means 51 from the air discharge port 35b of the container 35.

Molding material is set for a rotary type tabletting machine 41 and the machine 41 is driven.

Also an air suction means 71 for generating air flow and lubricant suction means 81 are driven.

The lubricant powder L sent to the lubricant spray means 51 passes through the penetrating hole 51h from the lubricant introduction port 51a together with air and sprayed at a blast on the upper surface S45 of the lower punch 45 inserted into a predetermined position in the die 43 positioned at a lubricant spraying point by the rotation of the rotary table 42 from the discharge port 51b.

Extra lubricant L piled on the upper surface S45 of the lower punch 45 is blown away from the upper surface S45 by air fed together with lubricant powder L and a part of the blown away lubricant is designed to be attached on the circumferential wall S43 of the die 43.

Further, the lubricant powder L is sent to opposite direction of rotation of the rotary table 42 through the pipe T formed by the combination of both the groove v provided on the surface (bottom) of the lubricant spray means 51 and the surface of the rotary table 42.

Lubricant powder L sent to the slit 51s provided for the lubricant spray means 51 via the pipe T moves to the suction port 71a of the air suction means 71 riding on upward air flow uniformly produced above the slit 51s by driving the air suction means 71 for generating air flow.

At this time lubricant powder L is attached on the lower surface S44 of the upper punch 44 which passes through the upper punch accommodating part 52 provided outside surface side of the slit 51s according to rotation of the rotary table 42.

When the die 43 sent downstream of the lubricant spraying point by the rotation of the rotary table 42 and the lower punch 45 also sent downstream of the lubricant spraying point so as to be synchronized with the rotation of the rotary table 42 pass under the suction port 81a of the lubricant suction means 81, lubricant powder attached around the dies 43 of the rotary table 42 and extra lubricant powder attached on the circumferential surface S43 of the die 43 and the upper surface S45 of the lower punch 45 are removed.

Next, at a material charge point, a mixture of active substance 2 affected by lubricant and adjuvant (except for lubricant) 3 is charged in the die 43 in which the lower punch 45 on which surface lubricant powder L is uniformly applied is inserted in a predetermined position and of which circumferential walls 43 is uniformly applied with lubricant powder L.

After extra mixture is scraped by a scraper, the mixture is compressed to be a tablet 1 by means of the upper punch 44 of which lower surface S44 is uniformly sprayed with lubricant powder L, the lower punch 45 on which upper surface S45 is uniformly sprayed with lubricant powder L, and the die 43 of which circumferential side walls S43 is uniformly sprayed with lubricant power L. Then thus produced tablet 1 is sequentially discharged at a tablet discharging point P2.

A part, or all in some cases, of the lubricant powder L applied on the surfaces of the punches 44, 45 and the dies 43 is transposed to the surface of the produced tablet 1 so that the tablet 1 shown in FIG. 1 is produced.

As the tablet 1 doesn't include lubricant 4 ••• therein, the active substance 2 ••• contained in the tablet 1 doesn't contact lubricant 4 •••. Therefore, if the active substance 2 ••• is affected by lubricant 4, such active substance 2 ••• doesn't touch lubricant 4 ••• in the tablet 1 at all even though the active substance 2 exposed on the surface of the tablet 1 may touch the lubricant 4. Therefore, the tablet 1 isn't colored or the potency of active substance 2 ••• isn't deteriorated so that the active substance 2 ••• can be kept stably for a long time.

As the mixture of active substance granule 2 ••• and adjuvant granule 3 ••• is compressed to be the tablet 1, not a mixture of active substance powder and adjuvant powder, active substance granule 2 ••• and/or adjuvant granule 3 ••• are deformed and destroyed while tabletted so that mechanical force applied in the tablet is dispersed.

Therefore, if the physical and chemical condition of the active substance 2 ••• are apt to be changed when high pressure is applied, the pressure at a time of compression doesn't concentrate on the active substance granule 2 ••• so that tabletting can be accomplished without making the active substance 2 ••• denatured.

In this embodiment because the particle diameters of the active substance granule 2 ••• and the adjuvant granule 3 ••• are substantially same, such granule can be homogeneously mixed in the course of nature in mixing process, as mentioned above. Further, when such mixture is charged in the die 43 into which the lower punch 45 is inserted into a predetermined position at the material charge point P1 of the rotary type tabletting machine during tabletting procedure, particle segregation of the active substance granule 2 ••• is appeared. Thus, the active substance granule 2 ••• is contained in the tablet 1 homogeneously so that such tablet is excellent as a dividable tablet.

Next, the present invention is explained with examples based on concrete data.

(Experiment 1)

Aspirin powder (Japanese Pharmacopoeia) was granulated to as to have a predetermined particle diameter by a well-known fluid bed granulation method by means of binder (hydroxypropyl cellulose was used in this experiment).

Particularly 9800 g of aspirin powder (Japanese Pharmacopoeia) was granulated so as to have a predetermined particle diameter by a well-known fluid bed granulation method by means of 200 g of binder (hydroxypropyl cellulose).

Thus granulated aspirin granule and adjuvant powder (lactose powder (Japanese Pharmacopoeia) was used in this experiment) are mixed.

More particularly 2000 g of thus granulated aspirin granule and 2000 g of adjuvant powder (lactose powder (Japanese Pharmacopoeia)) were mixed.

Then thus obtained mixture of aspirin granule and adjuvant powder were continuously tabletted by the tablet production system (tabletting machine with lubricant spray means) 11 as shown in FIG. 2.

In this experiment magnesium stearate was applied as lubricant on the surfaces of the punches 44 •••, 45 •••, and the dies 43 ••• of the tablet production system (tabletting machine with lubricant spray means) 11 and the mixture of aspirin granule and adjuvant powder was tabletted (compressed) by means of the punches 44 •••, 45 •••, and the dies 43 ••• on which surfaces magnesium stearate was applied.

(Experiment 2)

Aspirin powder (Japanese Pharmacopoeia) was granulated so as to have a predetermined particle diameter by a well-known fluid bed granulation method by means of binder (hydroxypropyl cellulose was used in this experiment).

Particularly 9900 g of aspirin powder (Japanese Pharmacopoeia) was granulated so as to have a predetermined particle diameter by a well-known fluid bed granulation method by means of 100 g of binder (hydroxypropyl cellulose (Japanese Pharmacopoeia)).

Adjuvant except for lubricant (lactose powder (Japanese Pharmacopoeia) was used) was granulated so as to have a predetermined particle diameter by a well-known fluid bed granulation method by means of binder (hydroxypropyl cellulose was used in this experiment).

More particularly 9900 g of adjuvant except for lubricant (lactose powder (Japanese Pharmacopoeia)) was granulated so as to have a predetermined particle diameter by a well-known fluid bed granulation method by means of 100 g of binder (hydroxypropyl cellulose (Japanese Pharmacopoeia)).

In this time the average particle diameter and particle size distribution of the aspirin granule and adjuvant granule were made almost same.

Thus granulated aspirin granule and adjuvant granule (lactose powder (Japanese Pharmacopoeia) was used in this example) were mixed.

More particularly 2000 g of thus granulated aspirin granule and 2000 g of adjuvant granule (lactose powder (Japanese Pharmacopoeia)) were mixed.

Then thus obtained mixture of aspirin granule and adjuvant granule were continuously tabletted by the tabletting machine with lubricant spray means 11.

In this experiment magnesium stearate was applied as lubricant on the surfaces of the punches 44 •••, 45 •••, and the dies 43 ••• of the tablet production system (tabletting machine with lubricant spray means) 11 and the mixture of aspirin granule and adjuvant granule was tabletted (compressed) by means of the punches 44 •••, 45 •••, and the dies 43 ••• on which surfaces magnesium stearate was applied.

(Comparison 1)

Aspirin powder (Japanese Pharmacopoeia) was granulated so as to have a predetermined particle diameter by a well-known fluid bed granulation method by means of binder (hydroxypropyl cellulose was used in this comparison).

Particularly 9800 g of aspirin powder (Japanese Pharmacopoeia) was granulated so as to have a predetermined particle diameter by a well-known fluid bed granulation method by means of 200 g of binder (hydroxypropyl cellulose).

After a fixed amount of lubricant (magnesium stearate in this embodiment) was added to the granulated aspirin granule and adjuvant powder (lactose powder (Japanese Pharmacopoeia) was used in this embodiment), and they were mixed.

More particularly 2000 g of thus granulated aspirin granule, 1960 g of adjuvant powder (lactose powder (Japanese Pharmacopoeia)), and 40 g of lubricant (magnesium stearate (Japanese Pharmacopoeia)) were mixed.

Then thus obtained mixture of aspirin granule, adjuvant powder, and lubricant were continuously tabletted by the well-known rotary type tabletting machine.

(Experiment 3)

Ascorbic acid powder (Japanese Pharmacopoeia) was granulated so as to have a predetermined particle diameter by a well-known fluid bed granulation method by means of binder (hydroxypropyl cellulose was used in this experiment).

Particularly 9800 g of ascorbic acid powder (Japanese Pharmacopoeia) was granulated so as to have a predetermined particle diameter by a well-known fluid bed granulation method by means of 100 g of binder (hydroxypropyl cellulose).

Thus granulated ascorbic acid granule and adjuvant powder (lactose powder (Japanese Pharmacopoeia) was used in this example) were mixed.

More particularly 2000 g of thus granulated ascorbic acid granule and 2000 g of adjuvant powder (lactose powder (Japanese Pharmacopoeia)) were mixed.

Then thus obtained mixture of ascorbic acid granule and adjuvant powder were continuously tabletted by the tablet production system (tabletting machine with lubricant spray means) 11 used in the experiment 1.

In this experiment magnesium stearate was applied as lubricant on the surfaces of the punches 44 •••, 45 •••, and the dies 43 ••• of the tablet production system (tabletting machine with lubricant spray means) 11 and the mixture of ascorbic acid granule and adjuvant powder was tabletted (compressed) by means of the punches 44 •••, 45 •••, and the dies 43 ••• on which surfaces magnesium stearate was applied.

(Experiment 4)

Ascorbic acid powder (Japanese Pharmacopoeia) was granulated so as to have a predetermined particle diameter by a well-known fluid bed granulation method by means of binder (hydroxypropyl cellulose was used in this experiment).

Particularly 9900 g of ascorbic acid powder (Japanese Pharmacopoeia) was granulated so as to have a predetermined particle diameter by a well-known fluid bed granulation method by means of 100 g of binder (hydroxypropyl cellulose).

Adjuvant except for lubricant (lactose powder (Japanese Pharmacopoeia) was used in this experiment) was granulated so as to have a predetermined particle diameter by a well-known fluid bed granulation method by means of binder (hydroxypropyl cellulose was used in this experiment).

More particularly 9900 g of adjuvant except for lubricant (lactose powder (Japanese Pharmacopoeia)) was granulated so as to have a predetermined particle diameter by a well-known fluid bed granulation method by means of 100 g of binder (hydroxypropyl cellulose).

In this time the average particle diameter and particle size distribution of the ascorbic acid granule and adjuvant granule were made almost same.

Thus granulated ascorbic acid granule and adjuvant granule were mixed.

More particularly 2000 g of thus granulated ascorbic acid granule and 2000 g of adjuvant granule were mixed.

Then thus obtained mixture of aspiring granule and adjuvant granule were continuously tabletted by the tablet production system (tabletting machine with lubricant spray means) 11 used in the experiment 1.

In this experiment magnesium stearate was applied as lubricant on the surface of the punches 44 •••, 45 •••, and the dies 43 ••• of the tabletting machine with lubricant spray means 11 and the mixture of ascorbic acid granule and adjuvant granule was tabletted (compressed) by means of the punches 44 •••, 45 •••, and the dies 43 ••• on which surfaces magnesium stearate was applied.

(Comparison 2)

Ascorbic acid powder (Japanese Pharmacopoeia) was granulated so as to have a predetermined particle diameter by a well-known fluid bed granulation method by means of binder (hydroxypropyl cellulose was used in this comparison).

Particularly 9800 g of ascorbic acid powder (Japanese Pharmacopoeia) was granulated so as to have a predetermined particle diameter by a well-known fluid bed granulation method by means of 100 g of binder (propoxyproyl cellulose (Japanese Pharmacopoeia)).

After a fixed amount of lubricant (magnesium stearate was used in this embodiment) was added to the granulated ascorbic acid granule and adjuvant powder (lactose powder (Japanese Pharmacopoeia) was used in this embodiment), and they were mixed.

More particularly 2000 g of thus granulated ascorbic acid granule, 1960 g of adjuvant powder (lactose powder (Japanese Pharmacopoeia)), and 40 g of lubricant (magnesium stearate (Japanese Pharmacopoeia)) were mixed.

Then thus obtained mixture of ascorbic acid granule, adjuvant powder, and lubricant was continuously tabletted by the well-known rotary type tabletting machine.

(Storage Test)

Each tablet obtained by the experiments 1–4 and comparisons 1, 2 was stored at 40° C. for six months. The content of principal agent (basis) (aspirin or ascorbic acid) after 6 month was measured.

The result is shown in Table 1.

| Sample | content of active substance |
|---|---|
| Experiment 1 | 99.5 |
| Experiment 2 | 99.7 |
| Comparison 1 | 95.3 |
| Experiment 3 | 99.4 |
| Experiment 4 | 99.6 |
| Comparison 2 | 95.8 |

In the table 1 the content of main principal (basis) (aspirin or ascorbic acid) after six months is shown as weight percent when the content of main principal included in the tablet at start time is 100.

From the result of the table 1, it was found that each tablet produced by the experiments 1–4 kept its main principal (basis) stably after 6 months comparing with each tablet in comparisons 1 and 2.

(Coloring Degree Test)

Each tablet obtained by the experiments 1–4 and comparisons 1, 2 was stored at 40° C. for six months. The coloring degree of the tablet after 6 month was measured.

It was found that ΔE (color difference) of each tablet obtained by the experiments 1–4 was 2 and below after 6 months, however, ΔE of each tablet in comparisons 1 and 2 was from 4 and above to 7 and below after 6 months comparing with the start time.

As a result it was found that each tablet obtained by the experiments 1–4 wasn't colored when being stored long time.

The same storage test and coloring degree test as mentioned above were executed for the tablet in which calcium stearate, hydrated aluminum silicate, or talc was used as lubricant in the experiments 1–4 and the comparisons 1 and 2. In any cases it was found that the same tendency as the experiments 1–4 and the comparisons 1 and 2 were shown.

Each granule of the experiments 1 and 2 was mixed with the same mixer under the same condition for the same time, and particle segregation of active substance granule in the mixture was visually examined. In the experiment 1 particle segregation was observed till the end of examination, however in the experiment 2, particle segregation wasn't seen as mixing time passed and active substance granule and adjuvant granule were uniformly mixed in the course of nature after mixing was executed for a predetermined time.

As for the experiments 1 and 2, active substance granule was colored and distribution of active substance granule in the produced tablet was visually examined. In the experiment 1, active substance granule was segregated, however in the experiment 2, such particle segregation of active substance granule wasn't observed.

Each granule of the experiments 3 and 4 was mixed with the same mixer under the same condition for the same time, and particle segregation of active substance granule in the mixture was visually examined. In the experiment 3 particle segregation was observed till the end of examination, however in the experiment 4, particle segregation wasn't seen as mixing time passed and active substance granule and adjuvant granule were uniformly mixed in the course of nature after mixing was executed for a predetermined time.

As for the experiments 3 and 4, active substance granule was colored and distribution of active substance granule in the produced tablet was visually examined. In the experiment 3, active substance granule was segregated, however in the experiment 4 such segregation of active substance granule wasn't observed.

In the above-mentioned experiments 1–4 aspirin and ascorbic acid were used. However, "active substance affected by lubricant" isn't limited to them. Such active substance includes active substance of which coloring degree after a fixed time when it is mixed with adjuvant except for lubricant and lubricant is larger than that when it is mixed with adjuvant except for lubricant comparing with the start of examination in case that stability test of active substance (such as severe test, long preservation test, acceleration test and so on) is executed for a mixture of active substance and adjuvant except for lubricant and a mixture of active substance, adjuvant except for lubricant and lubricant, coloring degree test (like absorbance analysis and color analysis) is executed, and content of active substance is measured. It also includes active substance of which content when it is mixed with adjuvant except for lubricant and lubricant is reduced comparing with that mixed with adjuvant except for lubricant after a fixed time from the start of examination.

INDUSTRIAL APPLICABILITY

As mentioned above, because the tablet of the present invention doesn't include lubricant therein, active substance contained in the tablet doesn't touch lubricant. Therefore, even if active substance contained in the tablet is affected by lubricant, the tablet isn't colored, or deteriorated in its potency.

According to the tablet of the present invention, because chemical substance having functional group doesn't touch lubricant in the tablet, the tablet isn't colored or deteriorated in its potency so that the tablet can show high stability.

According to the table of the present invention, as ascorbic acid or acetylsalicylic acid contained in the tablet doesn't touch lubricant in the tablet, the tablet isn't colored or its potency isn't deteriorated so that the tablet is kept stable.

According to the tablet of the present invention, as a mixture of active substance granule and adjuvant granule, not a mixture of active substance powder and adjuvant powder, can be compressed, such granule is deformed or broken so that mechanical force applied therein is dispersed.

Therefore, pressure of compression procedure isn't concentrated on the active substance granule so that active substance can be produced as tablet without being denatured even if the physical and chemical condition of active substance is denatured when high pressure is applied.

Further, particle diameters of active substance granule and adjuvant granule are substantially same so that such granule can be homogeneously mixed in the course of nature.

Furthermore, particle segregation of active substance granule isn't seen in the mixture when the mixture is charged in the die in which the lower punch is inserted into a predetermined position at a molding material charge point of the rotary type tabletting machine during compression procedure.

Therefore, active substance granule is homogeneously dispersed in the tablet.

Also such a tablet is excellent as a dividable tablet.

According to the tablet production method of the present invention, as lubricant isn't required to be added in molding material, a tablet without including lubricant can be easily produced if active substance included in the tablet is affected by lubricant.

Therefore, as lubricant isn't required to be added in molding material, a tablet which isn't colored or deteriorated in its potency can be easily produced if the active substance is affected by lubricant.

Further according to the tablet production method of the present invention, lubricant powder dispersed by positive pulsating vibration air is sprayed at a blast on the upper surface of the lower punch on which extra lubricant powder is apt to be adhered by gravitation and exposure time of the upper surface of the lower punch in lubricant powder is made short. And extra lubricant powder accumulated on the upper surface of the lower punch by gravitation is blown off so that lubricant powder can be applied on the upper surface of the lower punch uniformly.

A part of lubricant powder blown from the upper surface of the lower punch is designed to be attached on the circumferential wall of the die to which the lower punch is inserted to a fixed position. Almost the same amount of lubricant as that attached on the upper surface of the lower punch is uniformly attached on the circumferential wall of the die on which lubricant is difficult of attaching comparing with the upper surface of the lower punch.

Upward air flow is generated almost vertically against the lower surface of the upper punch around the lower surface of the upper punch on which lubricant is difficult of attaching by gravity.

Therefore, lubricant powder dispersed by positive pulsating vibration air collides with the lower surface of the upper punch and is attached thereon by riding on the upward air flow into the direction of the lower surface of the upper punch.

Further according to the production method of the present invention, the lower surface of the upper punch is designed to be exposed in lubricant powder longer comparing with the upper surface of the lower punch so that the same amount of lubricant powder as that for the upper surface of the lower punch and the circumferential wall of the die can be uniformly attached on the lower surface of the upper punch by adjusting the exposure time.

Thus according to the tablet production method of the present invention, as almost the same amount of lubricant powder is uniformly applied on the lower surface of the upper punch, the upper surface of the lower punch, and the circumferential wall of the die, molding material doesn't attach on the punches and the dies while tabletting if lubricant isn't added in molding material. As a result, griding between punches and dies of a molding machine while tabletting is prevented and tabletting problems such as sticking, laminating and capping of produced tablets are also prevented. Therefore, continuous tabletting of molding material can be achieved more completely and tablet without including lubricant therein can be produced at higher production efficiency.

Accordingly, if such tablet production method is used, tablet without including lubricant therein can be produced more easily and at higher production efficiency. Even if active substance included in the tablet is affected by lubricant, a tablet which isn't colored or of which active substance potency isn't deteriorated during storage of the tablet can be produced.

What is claimed is:

1. A lubricant tablet comprising:
    a compressed mixture of an active substance which is adversely affected by a lubricant and an adjuvant, said compressed mixture not containing said lubricant, wherein
    said lubricant is contained only on the surface of said tablet, wherein said tablet does not contain ascorbic acid and wherein said active substance is acetylsalicyclic acid.

2. A method for producing a lubricated tablet comprising the steps of:
    producing a mixture of an active substance affected by a lubricant admixed with an adjuvant, said mixture not containing said lubricant,
    dispersing a powder of said lubricant within positive pulsating vibration air,
    spraying said dispersed lubricant powder on a lower surface of an upper punch, an upper surface of a lower punch and an inner circumferential wall of a die in a tabletting machine, and
    tabletting said mixture within said lubricant upper and lower punches and die,
    wherein said tablet does not contain ascorbic acid and wherein said active substance is acetylsalicyclic acid.

3. The method for producing a tablet as set forth in claim 2, wherein said spraying step comprises:
    (i) spraying said dispersed lubricant powder substantially vertically onto said lower punch and said die when said lower punch attains a predetermined position in said die, and
    (ii) spraying said dispersed lubricant powder onto said lower surface of said upper punch while said upper punch travels along is moving path.

4. The tablet as set forth in claim 1, wherein
    said compressed mixture is an admixture of first and second granules, said first granules comprising said active substance and said second granules comprising said adjuvant, wherein
    said first and second granules have substantially same particle diameters.

5. The method as set forth in claim 2 or 3,
    said compressed mixture being an admixture of first and second granules, said first granules comprising said active substance and said second granules comprising said adjuvant, wherein
    said first and second granules have substantially same particle diameters.

6. A method for stabilizing an active substance in a tablet comprising the steps of:

selecting a combination of an active substance and a lubricant, wherein the active substance is affected by the lubricant when compressed in a form of a mixture of the active substance and the lubricant, producing a mixture of the selected active substance admixed with an adjuvant said mixture not containing the lubricant, dispersing a powder of said selected lubricant within positive pulsating vibration air, spraying said dispersed lubricant powder on a lower surface of an upper punch, an upper surface of a lower punch and an inner circumferential wall of a die in a tableting machine, and tabletting said mixture within the lubricant upper and lower punches and die, wherein said tablet does not contain ascorbic acid.

7. The method as set forth in claim 6, wherein said spraying step comprises:

(i) spraying said dispersed lubricant powder substantially vertically onto said lower punch and said dies when said lower punch attains a predetermined position in said die, and (ii) spraying said dispersed lubricant powder onto said lower surface of said upper punch while said upper punch travels along its moving path.

* * * * *

UNITED STATES PATENT AND TRADEMARK OFFICE
CERTIFICATE OF CORRECTION

PATENT NO.  : 6,764,695 B1
DATED       : July 20, 2004
INVENTOR(S) : Yasushi Watanabe et al.

It is certified that error appears in the above-identified patent and that said Letters Patent is hereby corrected as shown below:

Column 1,
Line 17, "a" should be deleted.

Column 2,
Line 32, "is" should read -- are --.

Column 3,
Line 11, "doesn't" should read -- don't --.

Column 6,
Line 21, "nternal" should read -- internally --;
Line 23, "include" should read -- includes --; and
Line 61, "are" should read -- is --.

Column 7,
Line 20, "with" should be deleted; and
Line 66, "the" should read -- that the --.

Column 12,
Line 30, "adjvant" should read -- adjuvant --.

Column 14,
Line 6, "are" should read -- is --;
Line 37, "was" should be deleted; and
Line 43, "were" should read -- was --.

Column 20,
Line 40, "lubricant" should read -- lubricated --; and
Line 52, "is" should read -- its --.

UNITED STATES PATENT AND TRADEMARK OFFICE
CERTIFICATE OF CORRECTION

PATENT NO.      : 6,764,695 B1
DATED           : July 20, 2004
INVENTOR(S)     : Yasushi Watanabe et al.

It is certified that error appears in the above-identified patent and that said Letters Patent is hereby corrected as shown below:

Column 21,
Line 8, "adjuvant" should read -- adjuvant, --;
Line 15, "tableting" should read -- tabletting --.

Column 22,
Line 7, "dies" should read -- die --.

Signed and Sealed this

Fourteenth Day of December, 2004

JON W. DUDAS
*Director of the United States Patent and Trademark Office*